(12) United States Patent
Margossian et al.

(10) Patent No.: US 9,642,391 B1
(45) Date of Patent: May 9, 2017

(54) ANTI-REGURGITATION COMPOSITION MAINTAINING GUT MOTILITY

(71) Applicant: UNITED PHARMACEUTICALS, Paris (FR)

(72) Inventors: Jonathan Albert Margossian, Paris (FR); Nicolas Pradeau, Tinteniac (FR)

(73) Assignee: UNITED PHARMACEUTICALS, Paris (FR)

( * ) Notice: Subject to any disclaimer, the term of this patent is extended or adjusted under 35 U.S.C. 154(b) by 0 days.

(21) Appl. No.: 15/399,767

(22) Filed: Jan. 6, 2017

Related U.S. Application Data

(63) Continuation of application No. 14/889,012, filed as application No. PCT/EP2014/059312 on May 7, 2014, now Pat. No. 9,554,587.

(30) Foreign Application Priority Data

May 7, 2013 (FR) ..................... 13 54200

(51) Int. Cl.
| | |
|---|---|
| *A61K 36/00* | (2006.01) |
| *A23L 33/00* | (2016.01) |
| *A23L 29/231* | (2016.01) |
| *A23L 33/105* | (2016.01) |
| *A23L 29/212* | (2016.01) |
| *A61K 36/48* | (2006.01) |

(52) U.S. Cl.
CPC ............. *A23L 33/40* (2016.08); *A23L 29/212* (2016.08); *A23L 29/231* (2016.08); *A23L 33/105* (2016.08); *A61K 36/48* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 2,949,428 | A | 8/1960 | Albert et al. |
| 3,433,650 | A | 3/1969 | Block et al. |
| 4,291,066 | A | 9/1981 | Anema et al. |
| 5,324,531 | A | 6/1994 | Hoefler et al. |
| 9,072,767 | B2 | 7/2015 | Margossian et al. |
| 2004/0258825 | A1 | 12/2004 | Ndife et al. |
| 2012/0213858 | A1 | 8/2012 | Thomas et al. |
| 2013/0309266 | A1 | 11/2013 | Margossian et al. |
| 2015/0202225 | A1 | 7/2015 | Margossian et al. |

FOREIGN PATENT DOCUMENTS

| | | |
|---|---|---|
| EP | 0 689 770 | 1/1996 |
| EP | 0 846 422 | 6/1998 |
| EP | 1 070 457 | 1/2001 |
| FR | 2 913 857 | 9/2008 |
| WO | WO 2009/065900 | 5/2009 |
| WO | WO 2010/120172 | 10/2010 |
| WO | WO 2012/080462 | 6/2012 |

OTHER PUBLICATIONS

Written Opinion in International Application No. PCT/EP2014/059312, Sep. 11, 2014, pp. 1-8.

*Primary Examiner* — Qiuwen Mi
(74) *Attorney, Agent, or Firm* — Saliwanchik, Lloyd & Eisenschenk

(57) ABSTRACT

The present invention relates to nutritional compositions intended to prevent or treat regurgitations in infants and young children without altering, or even improving, their gut motility and/or for preventing and/or treating intestinal disorders of the infant or child. The invention also concerns the process for manufacturing this composition.

11 Claims, 1 Drawing Sheet

A
| pH | Viscosity (cP) | Spindle/speed | T°C |
|---|---|---|---|
| 6.61 | 36 | S61/60 rpm | 37°C |
| 6 | 1502 | S62/12 rpm | 37°C |
| 5.5 | 645 | S62/30 rpm | 37°C |
| 5 | 420 | S62/30 rpm | 37°C |
| 4.5 | 326.9 | S62/60 rpm | 37°C |
| 4 | 180 | S62/60 rpm | 37°C |
| 3.5 | 145 | S62/60 rpm | 37°C |
B
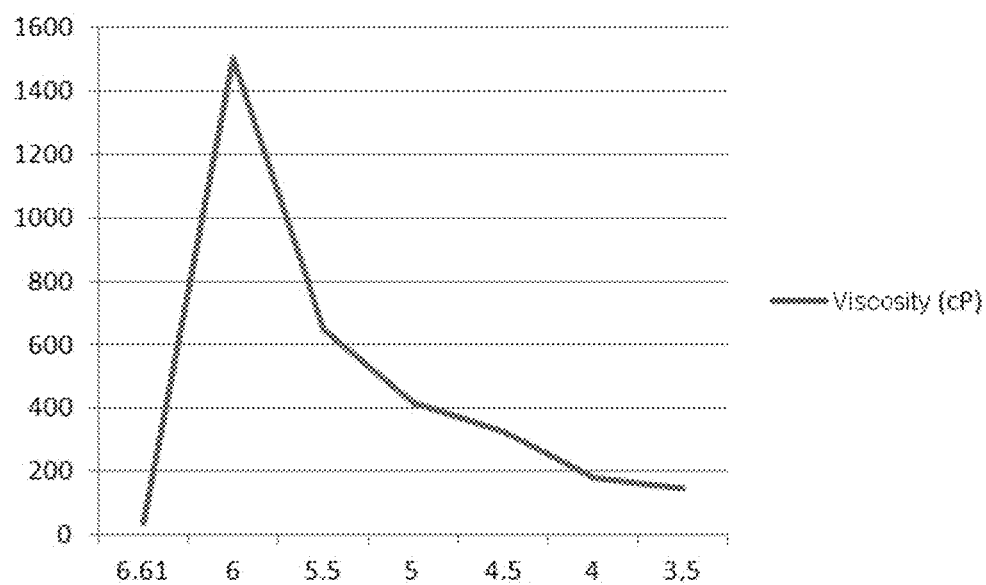

ANTI-REGURGITATION COMPOSITION MAINTAINING GUT MOTILITY

CROSS-REFERENCE TO RELATED APPLICATIONS

This application is a continuation of U.S. Ser. No. 14/889,012, filed Nov. 4, 2015, which is the U.S. national stage application of International Patent Application No. PCT/EP2014/059312, filed May 7, 2014.

FIELD OF THE INVENTION

The field of the present invention is that of medicine and human nutrition, in particular infant nutrition. The invention relates to nutritional compositions intended to prevent or treat regurgitations and/or gastroesophageal reflux in infants and young children without altering, or even improving their gut motility, typically by reducing or avoiding secondary effects (constipation, liquid stools, etc.) conventionally caused by the ingestion of infant milk with an anti-regurgitation purpose. It also relates to nutritional compositions intended to prevent and/or treat intestinal disorders of the infant or child.

The object of the invention is ideally to reduce, preferably suppress, regurgitation and/or reflux phenomena affecting a subject while maintaining his/her gut motility, i.e., by not causing any diarrhea or constipation. Compositions, formulae, preparations and anti-regurgitation and/or anti-reflux infant milks maintaining proper glut motility in infants and young children, in particular avoiding anomalies of gut motility described in the present text, are thus more particularly described.

PRIOR ART

Regurgitations are a symptom frequently observed in newborns and infants, resulting from an increase in abdominal pressure with respect to thoracic pressure. They often occur after meals or upon eructation phenomena. These regurgitations, which may also affect adults, and are distinguished in the medical sense of the term from vomiting, have no consequences on the development of the child and mainly indicate discomfort.

The mechanism of regurgitations may be explained in the following way: the lower esophageal sphincter is a circular muscle located in the lower portion of the esophagus. During meals, this muscle is relaxed so as to facilitate propulsion of the ingested foodstuffs (food bolus) into the stomach. The main function of this muscle is to prevent the return of the contents of the stomach towards the esophagus by means of its tonic constriction.

In infants, this muscle may be immature. It therefore cannot always support and compensate for the pressure exerted by the gastric contents. It then tends, during and after meals, to relax and allow small volumes of gastric liquid to flow up into the pharynx and to the mouth, via the esophagus: the regurgitations.

This phenomenon generally appears from the first weeks of life of the child. Physiological development factors which contribute to the occurrence of these regurgitations disappear, most often spontaneously, when the child reaches the age of 12 to 15 months (Vandenplas Y., Belli D. et al., Current concepts and issues in the management of regurgitation of infants: a reappraisal, Acta Pediatr 85: 531-534, 1996).

Regurgitations are often at the origin of the anxiety of the parents who, consequently, do not hesitate consulting a physician. The concerns vary in children from simple inconvenience caused by the reflux, up to pain (as the wall of the esophagus is irritated, this gives rise to burns or even to ulcerative lesions of the esophagus). These pains are sources of tears and often complicate the falling asleep of the child.

In certain cases, excessively frequent and/or prolonged reflux may be responsible for complications, defining, regardless of the age reached by the subject, a pathological gastroesophageal reflux (GOR, further identified in the present text by the term "reflux"). In infants and children in particular, pathological reflux may have more atypical esophageal and respiratory consequences: breaking of the length and weight growth chart, recurrent rhino-pharyngo-bronchitis, asthma, bronchiolitis, and anemia. It is estimated that regurgitations and reflux occur in about 75% of children less than one year old.

The treatment recommended by the European Society for Pediatrics, Gastroenterology, Hepatology and Nutrition (ES-PGHAN) consists of thickening of the food bolus. Indeed, it was proved with clinical tests that an increase in the viscosity of the gastric content may significantly reduce the frequency and volume of regurgitations. Drug therapies (prokinetic agents, antisecretory agents, etc.) are essentially reserved for pathological reflux.

Thickeners conventionally used for many years, like pre-cooked and/or pregelatinized starches or carob seed flour, for example, may be added, during the preparation of the baby bottle, to infant milk.

Pre-thickened infant milks, so-called "anti-regurgitation" (AR) milks, have been proposed for several years. These AR formulations already contain a thickener, selected from starches and carob gum, at the origin of the viscosity of the reconstituted milk and thus having an anti-regurgitation effect.

However, these milks have drawbacks: they very often have secondary effects on gut motility. Many cases of constipation or, on the contrary, too liquid and/or too frequent stools in children fed with AR infant milk have been reported.

It is assumed that these effects are due to the thickeners used: the preparations based on carob flour are known to cause abdominal pain, colic and diarrhea subsequent to the fermentation of carob in the colon (Cane et al., Arch Dis Child 1985, 60: 71-75). Carob induces frequent, liquid and gelatinous stools. Although rare, serious complications such as acute intestinal obstruction or necrotizing enterocolitis have been reported in premature and newly born infants (Vandenplas et al., "The Diagnosis and management of gastro-esophageal reflux in infants," Early Hum Dev 2005, 81: 1011-24). Liquid stools are also sources of anxiety for parents. The diarrhea may actually cause increased losses of water and electrolytes (sodium, potassium, bicarbonates) which may rapidly become a problem in young children by causing more or less severe dehydration and requiring rehydration.

Thickened infant milks with starch are rather known for causing problems of constipation.

Constipation may be defined by difficulties, delay or total absence of defecation, for two weeks or more, sufficient for causing significant distress in the subject who suffers from it (Baker et al., J. Pediatric Gastroenterol. Nutr. 1999, 29: 612-26). Indeed, the longer the delay of defecation, the more the expulsion of the stools will be difficult and painful, and sometimes at the origin of anal fissures in infants or children. This suffering, a source of discomfort when it is not a source of pain in infants and children, is also often a source of anxiety for parents who fear that this is the symptom of a serious medical problem. Constipation may also be characterized by the emission of hard stools, the hardness being easily evaluated by one skilled in the art with reference to the Bristol scale (types 1, 2 and 3 of said scale).

Novalac AR® is an example of milk thickened with starch (ingredients: skim milk, lactose, vegetable oils, starch, minerals, vitamins, L-cystine, taurine, choline bitartrate, inositol, anti-oxidant (tocopherols), and L-carnitine). This milk gives good results in terms of effect on regurgitations, but causes constipation problems in a certain number of children.

It might therefore be believed that an anti-regurgitation composition comprising starch and carob (known for inducing liquid stools, as explained above) would protect infants against the secondary effects induced on the stools by both types of thickeners respectively, the effects of the latter annihilating each other. This is not the case: a Novalac study also showed that nearly 18% of the children receiving a thickened formula with cold-soluble carob and starch (AR Digest®-ingredients: maltodextrins, vegetable oils, lactose, milk protein hydrolyzate, carob, glucose, starch, minerals, vitamins, anti-oxidant (tocopherols), taurine, inositol, and L-carnitine) had diarrheic stools (Qualinov Inquiry, Nutrition et Pédiatrie, January 2010, 4, 10).

Therefore, there exist a certain number of anti-regurgitation infant milks, but these milks have undesirable secondary effects on gut motility. At the present time no infant milk exists, typically no anti-regurgitation and/or anti-reflux infant milk, which allows the child to maintain his/her gut motility or, in other terms, which limits or prevents alteration (whatever it is) of this transit, even less which is capable of re-establishing normal transit when the latter is altered. The development of such a milk therefore proves to be a real need for improving the comfort of the child as well as that of his/her parents and allowing better observance of the diet treatment of regurgitations.

Advantageously, the inventors have developed a nutritional composition, in particular an anti-regurgitation and/or anti-reflux nutritional composition, which maintains and ideally restores gut motility, surprisingly and unexpectedly, and thus avoids subjecting the infant to the annoyances associated with alteration of said transit such as constipation, soft stools, liquid and/or too frequent stools (diarrhea), and/or colic.

SUMMARY OF THE INVENTION

The object of the invention is a nutritional composition, typically an anti-regurgitation and/or anti-reflux composition (designated below more generally as an "anti-regurgitation nutritional composition" or "anti-regurgitation composition"), for infants or children, which preferably alters less than the compositions of the prior art and ideally does not alter the gut motility of said infant or child, or in other words allows preserving his/her gut motility and therefore limiting or reducing, ideally avoiding, constipation, soft stools, liquid stools, too frequent stools and/or colics, preferably constipation, soft stools, liquid and/or too frequent stools. In a particular embodiment, the composition according to the invention is, independently of its anti-regurgitation and/or anti-reflux action, capable of restoring gut motility in infants or children suffering from annoyances associated with an alteration of said transit. This composition comprises cold-soluble carob and pectins, preferably cold-soluble carob and at least two pectins of different natures.

The compositions according to the invention, notably the anti-regurgitation (and/or anti-reflux) compositions, advantageously have a viscosity of at least 150 mPa·s (i.e., at least 150 centipoises or 150 cP), preferably of at least 300 mPa·s, still more preferentially of at least 600 mPa·s, from pH=6, at a temperature comprised between 35 and 40° C., typically of about 37° C.

These compositions allow reducing or avoiding at least one, preferably at least two, still more preferentially all of the following intestinal disorders: constipation, soft stools, liquid and/or too frequent stools (diarrhea), and colic.

Advantageously, the viscosity is evaluated by means of a viscosimeter of the Brookfield (DV-I Prime) type at a temperature comprised between 35 and 40° C., typically of about 37° C., with a cylinder-shaped module S61 or a disc-shaped module S62 and rotary speeds varying from 12 to 100, for example from 20 to 100, revolutions per minute (rpm) depending on the measured viscosity values.

It is also possible to measure the time of flow of a constant volume of product through a calibrated orifice.

Typically, for viscosity values above 0 mPa·s and less than 100 mPa·s, the viscosity is evaluated with an S61 mobile at 60 rpm (revolutions per minute). For viscosity values greater than or equal to 100 mPa·s and less than 500 mPa·s, the viscosity is evaluated with an S62 mobile at 60 rpm. For viscosity values greater than or equal to 500 mPa·s and less than 999.8 mPa·s, the viscosity is evaluated with an S62 mobile at 30 rpm. For viscosity values greater than or equal to 998 mPa·s and less than 2,500 mPa·s, the viscosity is evaluated with an S62 mobile at 12 rpm.

In the composition according to the invention, the cold-soluble carob concentration is advantageously less than or equal to about 1% by weight, preferably less than or equal to 0.75% by weight, for example 0.5% by weight, based on the total weight of the composition. All the weight percentages mentioned in the present description are expressed with reference to the total weight of the composition in which they are present.

The pectins used in the composition advantageously are highly esterified pectins, weakly esterified pectins (preferably amidated and weakly esterified pectins) or a mixture of both. According to a particularly preferred embodiment, the pectins used of different natures are a mixture of highly esterified pectins and of weakly esterified pectins, typically highly esterified pectins and amidated and weakly esterified pectins.

In a particular embodiment, the composition comprises cold-soluble carob, at least two pectins of different natures, and optionally starch, typically pre-cooked and/or pregelatinized starch.

In a particular embodiment, the composition according to the invention further comprises one or several ingredients selected from carbohydrates, said carbohydrates being preferably selected from lactose; maltodextrins; lipids; proteins, said proteins being hydrolyzed or non-hydrolyzed; and/or amino acids.

In another particular embodiment, the composition comprises cold-soluble carob at a concentration of less than about 0.75% by weight, preferably comprised between 0.2% and about 0.75% by weight, still more preferably of about 0.5%, and preferably starch at a concentration comprised between about 1% and about 10% by weight, typically between about 1% and about 5% by weight, said concentrations being expressed by weight based on the total weight of the composition.

In another further particular embodiment, the preceding composition further comprises lactose at a concentration comprised between about 20 and about 25% by weight, and/or maltodextrins at a concentration comprised between about 15 and about 30% by weight.

The composition, the object of the invention, may be both a powder or a liquid form. Advantageously it is a pasteurized powder or a sterile liquid.

A particular object of the invention thus relates to a composition according to the invention for use in infant milk, a food supplement for infants, a follow-up milk, a growth milk, or a dietetic food, typically a dietetic food for infants or children.

A particular composition of the invention is a dietetic food intended for special medical purposes, in particular an infant milk, typically an anti-regurgitation and/or anti-reflux infant milk, preferably allowing maintaining (not altering) the gut motility of the infant or child, or even restoring gut motility in infants or children suffering from annoyances associated with an alteration of said transit. The liquid base used for its preparation is typically a liquid base of a dietetic food intended for special medical purposes, in particular a liquid base of an infant milk.

The compositions according to the invention are particularly suitable for use in infants or children to whom an inhibitor of proton pumps (IPP) is administered, for example selected from omeprazole, esomeprazole, lansoprazole, pantoprazole and rabeprazole.

Another object of the invention relates to a method for preparing a nutritional composition of interest, typically an anti-regurgitation and/or anti-reflux nutritional composition, for infants or children, being a powder, which preferably is a composition not altering gut motility or allowing it to be maintained or restored. This method comprises the steps of:

a) preparing a liquid composition base, the dry material content of which being of at least 20% by weight based on the total weight of said composition, by mixing, with stirring, at a temperature of at least 60° C., constitutive elements of said composition, said elements comprising at least two pectins of different natures, advantageously at least one highly methylated pectin and at least one weakly methylated pectin (preferably at least one amidated and weakly methylated pectin), and cold-soluble carob, the cold-soluble carob concentration being less than or equal to about 1% by weight based on the total weight of said composition, b) homogenizing the liquid base obtained at the end of step a) by fractionation of the constitutive elements during a first step i) carried out under a pressure comprised between 100 and 300 bars and during a step ii) carried out under a pressure comprised between 10 and 60 bars, c) drying by atomization of the mixture obtained at the end of step b), and d) recovering the composition obtained at the end of step c) as a powder.

The composition, for example the anti-regurgitation and/or anti-reflux composition, thereby obtained is typically a dietetic food intended for special medical purposes, in particular an infant milk, for example an anti-regurgitation and/or anti-reflux infant milk, which preferably does not alter gut motility and allows maintaining it or restoring it when it is altered, and the liquid base which is used for preparing it is typically a liquid dietetic food base intended for special medical purposes, in particular a liquid base of infant milk.

In a preferred embodiment, the constitutive elements of the composition further comprise pre-cooked and/or pre-gelatinized starch.

In another particular embodiment, the dry material content of the liquid base is of at least 35% by weight based on the total weight of the liquid base.

In a particularly preferred embodiment, the preparation method further comprises a step for applying to the liquid base obtained at the end of step a) or at the end of step b) a heat treatment at a temperature comprised between 60° C. and 110° C. for a sufficient time in order to pasteurize said base, and allowing recovery of an anti-regurgitation and/or anti-reflux pasteurized composition as a powder at the end of step d).

In another embodiment, the preparation method comprises a step for preparing the liquid base produced with stirring at a temperature comprised between about 60° C. and about 90° C., and maintained with stirring until the homogenization step.

In further another embodiment, the homogenization step i) is advantageously carried out under a pressure comprised between about 170 bars and about 200 bars and the homogenization step ii) is advantageously carried out under a pressure comprised between about 30 bars and about 40 bars.

Another object of the invention relates to a composition, in particular an anti-regurgitation and/or anti-reflux composition, characterized in that it maintains the gut motility of the infant or child, for combined use in the treatment of regurgitation and prevention of gut motility anomalies or disorders (constipation, soft stools, diarrhea and/or colic, preferably hard stools, soft or liquid stools and/or too frequent stools) of the infant or child or for use in the prevention of gut motility anomalies or disorders of infants or children.

Further, another object of the invention relates to a composition, typically an anti-regurgitation and/or anti-reflux composition, characterized in that said composition restores gut motility of infants or children, for combined use in the treatment or prevention of regurgitation and/or reflux, as well as of anomalies or disorders of gut motility (constipation, soft stools, diarrheas and/or colic, preferably hard stools, soft or liquid stools and/or too frequent stools) of infants or children or for the sole treatment or the sole prevention of anomalies or disorders of gut motility (constipation, soft stools, diarrheas and/or colic, preferably, hard stools, soft or liquid stools and/or too frequent stools) of infants or children (i.e., independently of any treatment or prevention of a regurgitation and/or reflux problem).

DETAILED DESCRIPTION OF THE INVENTION

Nutritional compositions, such as anti-regurgitation infant milks, including carob and/or starch as thickener(s) have unpleasant secondary effects on gut motility (intestinal transit), in particular of infants (from birth to one year old), for which the fragile and immature digestive systems make them particularly sensitive, as well as of young children (three years old or less).

At the present time, no infant milk exists, typically having an efficient anti-regurgitation effect, which does not alter the gut motility of the subjects which ingest it, typically that of pre-identified subjects, in particular causing diarrhea.

The object of the invention is to specifically meet this need by describing a composition, typically an anti-regurgitation and/or anti-reflux nutritional composition, which limits alteration of, preferably does not alter, still more preferably maintains, or even restores, the gut motility of the subject to which it is administered.

The object of the invention is a nutritional composition, in particular an anti-regurgitation and/or anti-reflux nutritional composition for infants or children, which preferably alters less than the compositions of the prior art, and ideally does not alter, the gut motility of said infant or child, or in other words allows maintaining his/her gut motility and therefore limiting or reducing, ideally avoiding, constipation, soft stools, liquid stools, too frequent stools and/or colic, preferably constipation, soft stools, liquid stools and/or too frequent stools.

Within the scope of the present invention, the expression "anti-regurgitation composition" refers to a composition which neither causes regurgitations or gastro-esophageal reflux, preferably which limits regurgitations or gastro-esophageal reflux and ideally which prevents or inhibits regurgitations or gastro-esophageal reflux.

A composition which "maintains gut motility" refers to a composition which alters less than the known compositions of the prior art, and preferably does not alter, gut motility, typically does not alter gut motility of 90% of the infants or children from a tested population, typically which does not cause any undesirable effects on the stools, such as constipation, diarrhea, soft and/or liquid stools and/or too frequent stools, and/or colic.

The consistency of the stools may be evaluated by means of different scales, known to one skilled in the art, for example the Bristol scale, defined as follows:

Type 1: Hard and fragmented stools (in beads) difficult to pass
Type 2: Hard, sausage-shaped molded and lumpy stools
Type 3: Hard, sausage-shaped molded stools with a cracked surface
Type 4: Soft stools but molded as a sausage (or a snake)
Type 5: Fragmented soft stools with clear-cut edges and easy to pass
Type 6: Fragmented soft stools with ragged edges
Type 7: Totally liquid stools Within the context of the present invention, the so called "hard" stools correspond to types 1, 2 and 3 of the Bristol scale. So-called "formed or normal" stools correspond to types 4 and 5, so-called "soft" stools correspond to type 6 and so-called "liquid" stools correspond to type 7 of this same scale.

The term "diarrhea" is typically used for referring to soft and/or liquid and/or too frequent stools, for example the emission of at least three, typically at least four soft and/or liquid stools daily, preferably of at least five soft and/or liquid stools per day.

Within the scope of the present invention, the expression "restore gut motility" typically refers to the effect consisting of re-establishing normal transit when the latter is altered, in particular the effect consisting of re-establishing normal gut motility in subjects suffering from constipation, soft stools, liquid stools, soft to liquid stools, too frequent stools and/or colic, preferably in subjects suffering from constipation, diarrhea, hard, soft and/or liquid stools. Therefore the matter in particular is to normalize the consistency of the stools in subjects for which the stools are hard, soft or liquid, preferably so as to obtain formed stools.

The composition, the object of the invention, comprises cold-soluble carob and several pectins, preferably at least two pectins of different natures.

The native carob gum is a carob which has low solubility in an aqueous medium on the order of 20% at a temperature comprised between 10° C. and 45° C. (cf. patent application FR 2 913 857). The expression "solubility in an aqueous medium at a temperature comprised between 10° C. and 45° C." means that at a temperature comprised between 10° C. and 45° C., in an aqueous medium, the carob gum develops at least 20% of the viscosity which it would have developed if it had been put into solution at temperatures above 80° C. This carob form thus does not have satisfactory solubility in an aqueous medium, at the temperature of reconstitution of milk in the baby bottle (which is between about 30° C. and 50° C.). As such a solubility is, however, required preliminary to any homogeneous increase of viscosity, one tried to develop carobs said to be "cold-soluble" for which a large proportion of the viscous potential is already expressed between 30 and 50° C. The "cold-soluble" carob gum is on the contrary a carob which has solubility in an aqueous medium of more than 60% at a temperature comprised between 10° C. and 45° C. according to the definition given above.

The so-called "cold-soluble" carob is distinguished from native carob, notably in that it has a lower average molecular weight of carob than that of native carob. This particular weight average molecular weight may for example be obtained by breaking the glycoside bonds with the purpose of producing shorter chains. Such a cold-soluble carob may for example be obtained with the following process:

(i) the endosperm of native carob gum is hydrated;
(ii) it is proceeded with simultaneous drying and milling of the hydrated endosperm; and
(iii) at the end of step (ii), the average molecular weight of carob is reduced by a reaction of depolymerization of the latter.

Depolymerization of carob may for example be carried out by oxidation, via an enzymatic route, by acid hydrolysis, under the effect of high pressures and temperatures and in the presence of an oxidizer, or by physical treatments such as for example exposure to radiation of the gamma type.

The cold-soluble carob according to the invention advantageously has an average molecular weight ($\overline{M}_\omega$) comprised between $2.5 \cdot 10^5$ and $1.5 \cdot 10^6$ g/mol, preferably between $2.5 \cdot 10^5$ and $1 \cdot 10^6$ g/mol, still preferably between $2.5 \cdot 10^5$ and $6 \cdot 10^5$ g/mol.

"Cold-soluble" carobs are known to cause a rapid increase in the viscosity of the base of liquid milk, so that in the mind of one skilled in the art, the application of certain technological treatments, such as the application of a heat treatment (during the pasteurization or sterilization step), homogenization and atomization (spraying) required for producing a food powder, in particular infant milks in pasteurized powder form, are considered by one skilled in the art as impossible to apply in the presence of carob. Up to now, cold-soluble carob was only used as a dry and non-liquid mixture which had the drawback of not allowing systematic removal of the pathogenic bacteria which may contaminate the composition, said removal only being allowed by the application of a sterilization or pasteurization step applied to a liquid mixture.

It should be noted that for milk, in particular infant milk, the tolerated maximal total flora should preferably not exceed 1,000 UFCs (unit forming colonies) per gram of powder. Among this flora, *Clostridium perfringens, Escherichia coli, Bacillus cereus, Listeria monocytogenes*, Staphylococci with coagulase +, salmonellae and enterobacteria (notably *Cronobacter sakazakii*) are in particular considered pathogenic for human beings and should preferably be totally removed.

The process according to the invention now allows suppression of all pathogenic bacteria (in particular the bacteria listed earlier) for human beings, in particular for infants and children, notably young children.

The inventors have developed and now describe a composition, in particular an anti-regurgitation and/or anti-reflux composition, surprisingly having a very efficient anti-regurgitation and/or anti-reflux effect, said composition comprising cold-soluble carob and preferably pectins, still more preferentially cold-soluble carob and at least two pectins of different natures, and said composition being obtained by means of a process which allows the technical constraints known to one skilled in the art to be overcome, while allowing significant progress in terms of food safety.

The composition, the object of the invention, includes cold-soluble carob. Preferably, the composition, the object of the invention, comprises cold-soluble carob at a concentration of less than or equal to 1% by weight based on the total weight of the composition. Still more preferably, the composition comprises cold-soluble carob in a concentration comprised between about 0.2% and about 0.75% by weight based on the total composition weight, preferably about 0.5% by weight.

Advantageously, the composition, the object of the invention, also includes pectins, typically at least two pectins of different natures.

Within the context of the present invention, the terms "pectin" and "pectin substance" are used equally. Pectin substances are polymers of acid polysaccharides. They consist of a main chain consisting of uronic acid monomers bound in 1-4 between which rhamnose molecules are inserted with bonds 1-2 and 1-4 responsible for the zig-zag shape of the pectin macromolecules. These complex molecules have branches at the uronic acids and at the rhamnose with molecules of the galactan, rhamnan type, etc.

There exist a great variety of pectins, the origins of which are exclusively vegetable origins. Pectins are present in large amounts in the pips and peels of currants, apples, quinces and citrus fruit.

Pectins may form a network, thereby having a gelling effect. These compounds are very frequently used in nutritional preparations such as jams, precisely for these gelling properties.

Pectins are known to be stabilizers or thickeners (by increasing the viscosity) of nutritional compositions and notably of infant milks (US2003/0165606).

They are also used against diarrhea (Howard P, Pectin-agar for diarrhea in infants and the newborn, JAMA, 1940, 114(24): 2355-2358).

A drug, known for several decades, sold in pharmacies under the name of Gelopectose®, is moreover used for thickening the contents of the stomach.

As indicated earlier, the pectins used in the composition according to the invention are advantageously of different natures. According to a particular embodiment, pectins of different natures are selected from highly esterified pectins, weakly esterified pectins, amidated and weakly esterified pectins, and the mixture of at least two, for example all, of them. According to a particularly preferred embodiment, the pectins used of different natures are a mixture of highly esterified pectins and weakly esterified pectins, notably amidated and weakly esterified pectins.

"Highly esterified" pectins are typically highly methylated pectins (further identified in the present text as "HM" pectins).

"Weakly esterified" pectins are typically weakly methylated pectins (further identified in the present text as "LM" pectins).

Pectins are complex polymers present in the cell membranes of plants. Pectins consist mainly of galacturonic acid, for which the carboxyl group is frequently methylated. Other sugars such as rhamnose, galactose and arabinose may also be present, depending on the source plant and the extraction method.

"Weakly esterified" pectins used within the scope of the present invention are typically pectins from citrus fruit.

In a preferred embodiment, the composition has both weakly esterified pectins (preferably weakly methylated) and highly esterified pectins (preferably highly methylated). In a still more preferred embodiment, the weakly esterified pectins are amidated.

The amidation degree of the "amidated and weakly esterified pectins" present in the composition according to the invention is comprised between about 5% and about 30%, preferably between about 5% and about 20%, more preferentially between about 10% and about 20%. The amidation degree refers to the percentage of galacturonic acids bearing an amide group within a pectin molecule.

Its esterification degree, typically methylation degree, is typically comprised between about 20% and about 50%, preferentially between about 30% and about 50%, and more preferentially between about 30% and about 40%. The esterification degree refers to the percentage of methyl-esterified galacturonic acids within a pectin molecule.

When the composition according to the invention is for example an infant milk, the presence within this composition of at least one weakly esterified pectin, preferably of at least one amidated and weakly esterified pectin, allows obtaining a reconstituted infant milk (after dissolution of the powder in water) having low viscosity, typically a liquid milk having a viscosity comprised between 20 and 50 mPa·s at a reconstitution pH.

A reconstituted milk from a milk as a powder according to the invention, typically an anti-regurgitation milk as a powder according to the invention, has a particularly suitable viscosity, in the stomach, from pH=6, and more generally at a pH comprised between 6 and 5, for example between 5.8 and 5.5, typically at a pH of 5.2, 5.3, 5.4, 5.5, 5.6 or 5.7.

Moreover, the pH required for developing satisfactory viscosity in the sense of the invention is significantly greater for the composition according to the invention at the required pH of about 3.5 for conventional anti-regurgitation compositions. Thus, as the gastric pH gradually decreases after a meal from 7 to about 3, the product according to the invention develops viscosity more rapidly in the stomach than the conventional anti-regurgitation milks, and thereby allows limitation or even suppression of the regurgitation or reflux symptoms when they are present. Further, it is easy to drink through the teat of the baby bottle and allows the subject to be fed without any frustration while limiting the risks of aerophagia.

The desired optimum viscosity of the infant milk according to the invention, in particular of the anti-regurgitation and/or anti-reflux infant milk according to the invention, is preferably less than about 50 mPa·s as measured at a reconstitution pH (i.e., a pH of about 7) and at a temperature comprised between 35° C. and 40° C., and greater than about 150 mPa·s, preferably than about 500 mPa·s, still more preferentially comprised between about 500 and about 600 mPa·s, when it is measured at pH=5.5, and at a temperature also comprised between about 35° C. and about 40° C. (cf. FIG. 1).

The desired optimum viscosity of the infant milk according to the invention, in particular of the anti-regurgitation and/or anti-reflux infant milk according to the invention, is preferably less than 50 mPa·s measured at a reconstitution pH (of about 7) and at a temperature comprised between about 35° C. and about 40° C., and greater than about 150 mPa·s, preferably than about 600 mPa·s, even more preferentially comprised between about 800 and about 1,600 mPa·s, for example 1,500 mPa·s, when it is measured at pH=6, and at a temperature also comprised between 35° C. and 40° C. (cf. FIG. 1).

In the compositions according to the invention, typically in anti-regurgitation and/or anti-reflux infant milks, the pectins, typically said "at least two pectins of different natures", are present at a concentration of less than or equal to about 10% by weight based on the total weight of the composition, typically comprised between about 4% and about 10% by weight based on the total weight of the composition, for example about 5% by weight based on the total weight of the composition.

In the compositions according to the invention, typically in the anti-regurgitation and/or anti-reflux infant milks, the "weakly esterified pectin" is present at a concentration for example comprised between about 1% and about 10% by weight based on the total weight of the composition, preferably between about 2% and about 8%, for example between about 3% and about 8%, still more preferably between about 3% and about 5%, and typically of about 4%.

Advantageously, the concentration, within a composition according to the invention, of weakly esterified pectin and optionally of strongly esterified pectin will be adapted to the nature and the amount of the proteins possibly present in the composition.

Advantageously, the concentration, within a composition according to the invention, of weakly esterified pectin, in particular of amidated and weakly esterified pectin, will be all the higher since said composition will be rich in hydrolyzed proteins, and conversely, this concentration will be all the lower since said composition will be rich in non-hydrolyzed proteins.

The "highly esterified" pectins which may be used within the scope of the present invention are typically pectins of citrus fruit, in particular non-amidated pectins of citrus fruit.

The inventors discovered that such a "highly esterified pectin" used in combination with at least one "weakly esterified pectin", preferably with at least one "amidated and weakly esterified pectin", allows improving the stability of the composition according to the invention, typically of the anti-regurgitation and/or anti-reflux composition according to the invention (in particular the stability of the proteins), at acid pH.

The esterification degree, typically methylation degree, of the "highly esterified pectin" present in the composition according to the invention is comprised between about 50% and about 90%, preferably between about 50% and about 80%, more preferentially between about 60% and about 70%.

The stability index of said pectin at pH=4 is comprised between 140-200, preferably between about 150 and about 190, more preferentially between about 165 and about 185. This index, comprised between 100 and 200, is a measurement by sedimentation of the highly esterified pectin's capability of protecting non-hydrolyzed proteins in an acid medium of the flocculation and/or coagulation.

In the nutritional compositions according to the invention, typically in the anti-regurgitation and/or anti-reflux compositions, in particular maintaining gut motility or allowing it to be restored, the "highly esterified pectin" is advantageously present at a concentration comprised between about 0.1% and about 10% by weight based on the total weight of the composition, preferably between about 0.1% and about 5%, more preferentially of about 1%.

Preferably, the concentration of highly esterified pectin within a composition according to the invention comprising at least one weakly esterified pectin, preferably at least one amidated and weakly esterified pectin, and at least one highly esterified pectin, will be all the higher since said composition will be rich in non-hydrolyzed proteins, and conversely, this concentration will be all the lower since said composition will be rich in hydrolyzed proteins and/or amino acids in the mixture.

In a particular composition according to the invention, the concentration of non-hydrolyzed proteins is comprised between about 10 and 13% by weight based on the total weight of the composition, that of weakly esterified pectin, typically that of amidated and weakly esterified pectin, is comprised between 4 and 5% (for example 4.5%) and that of highly esterified pectin is of about 1%.

In a particular composition according to the invention, the concentration of hydrolyzed proteins is comprised between about 10% and about 13% by weight, that of weakly esterified pectin, typically that of amidated and weakly esterified pectin, is about 5% by weight, and that of highly esterified pectin is of about 1% by weight based on the total weight of the composition.

In a particular composition according to the invention, the concentration of non-hydrolyzed proteins is comprised between about 8% and about 10% by weight (typically of about 9% by weight), the concentration of hydrolyzed proteins is comprised between about 2% and about 4% by weight (typically of about 3% by weight), that of weakly esterified pectin, typically that of amidated and weakly esterified pectin, is comprised between about 4 and about 4.5% by weight (for example, 4.25%), and that of highly esterified pectin is of about 1% by weight based on the total weight of the composition.

The composition, the object of the invention, may also comprise starch.

The starch consists of amylose, a linear polymer of glucose bound through a 1-4 bonds, and amylopectin, a branched polymer of glucose containing both predominant a 1-4 bonds and a 1-6 branches. Depending on the plant source from which it is extracted, starch has a composition a little different in amylose and amylopectin.

Salivary alpha-amylase is not functional at birth. Its activity at the age of 3 months is clearly less than that of an adult. Also, the activity of this enzyme at the pancreas level gradually increases up to the age of 3 years. However, the gluco-amylase which is not very involved in adults in the digestion of starch is highly active from birth. This different distribution of the enzymatic activities allows the newly born to digest up to 3 g/kg/d of starch. The starch has the characteristic of having its structure modified under the effect of heat and hydration. Different forms of starches are distinguished, such as starch paste or starch gel in which solubilization leads to an increase in viscosity and an improvement of digestibility. These facts justify its use only as a pre-cooked or pre-gelatinized starch form in anti-regurgitation milks. Moreover, digestibility of starch is better when the latter includes a larger amount of amylopectin.

Starches, in association with proteins, in particular caseins, which flocculate at an acid pH, develop, in the stomach, the sought viscosity of the food bolus and thus allows reducing or avoiding regurgitations and reflux by the effect of gravity.

In an embodiment, the nutritional composition, the object of the invention, includes starch at a concentration of less than or equal to 5% by weight based on the total weight of the composition. Preferably, the composition includes starch at a concentration of less than or equal to 2.5% by weight based on the total weight of the composition. Also preferably, the composition includes starch at a concentration of less than or equal to 1% by weight based on the total weight of the composition. In another particularly preferred embodiment, the composition according to the invention does not comprise any starch.

An object of the invention is therefore a nutritional composition, typically an anti-regurgitation and/or anti-reflux composition, in particular maintaining gut motility or allowing restoring gut motility, comprising in weight percentages based on the total weight of the composition: about 1% of cold-soluble carob, preferably between about 0.2% and about 0.75%, still more preferentially about 0.5% of cold-soluble carob; between about 4% and about 5% of weakly esterified and amidated pectins; and about 1% of highly esterified pectins.

In a particular embodiment, the composition, the object of the invention, further comprises starch, preferably pre-cooked and/or pregelatinized starch.

Thus, in another embodiment of the invention, the nutritional, typically an anti-regurgitation and/or anti-reflux composition, in particular maintaining gut motility or allowing it to be restored, comprises in weight percentages based on the total weight of the composition: about 1% of cold-soluble carob, typically less than 1%, preferably between about 0.2% and about 0.75%, still more preferentially about 0.5% of cold-soluble carob; between about 4% and about 5% of weakly esterified and amidated pectins (typically weakly methylated); about 1% of highly esterified pectins (typically highly methylated); and optionally between about 0.5% and about 5% of starch, preferably about 1% of starch.

In another embodiment of the invention, the nutritional composition according to the invention, typically an anti-regurgitation and/or anti-reflux composition, in particular maintaining gut motility or allowing gut motility to be restored, further comprises about 26% of maltodextrins and about 22% of lactose, expressed by weight based on the total weight of the composition.

A particular object of the invention is an infant milk, for example an anti-regurgitation and/or anti-reflux milk, which does not alter the gut motility of the infant or child and therefore does not cause any effects on stools, or allows the gut motility to be restored. This infant milk is obtained from the composition described earlier comprising cold-soluble carob and pectins, typically at least two pectins of different natures.

An infant milk, typically an anti-regurgitation and/or anti-reflux milk, according to the present invention may comprise any base of infant milk known to one skilled in the art. Thus, any base of infant milk, for which the nutritional properties are adapted to the need of infants and children, including dietetic food intended for special medical purposes (DFSMP), may be used for preparing a composition according to the present invention.

A standard infant milk base comprises carbohydrates, lipids, proteins, minerals, vitamins and optionally growth factors. The customary proportions of these different constituents within the milk base are of about 55% for carbohydrates, 25% for lipids, 15% for proteins and 5% for the whole formed by the minerals and vitamins, the percentages being calculated with respect to the total weight (or the total mass) of dry material of the dehydrated milk base.

The milk base may further optionally comprise other compounds known to one skilled in the art, such as compounds improving the texture of the milk, the taste of the milk and/or having a specific nutritional or functional benefit (nucleotides, probiotics, prebiotics, etc.).

Conventionally, the protein fraction of the infant milk base may comprise two types of proteins: proteins of animal origin, notably those from milk (casein and/or soluble proteins, also called lactoserum proteins), and proteins of plant origin. The protein fraction may however advantageously comprise only one of these two types of proteins, for example only plant proteins.

Proteins of animal origin may for example stem from cow milk, goat milk, human milk, camel milk, buffalo milk, donkey milk and/or mare milk.

Proteins of plant origin may for example stem from rice, soya, peas, maize, wheat and/or potato.

The proteins present in the infant milk base, used within the scope of the present invention, may be whole, or on the contrary, totally or partly hydrolyzed proteins. This may also be a mixture of two types of proteins, for example comprising 75% whole proteins for 25% of hydrolyzed proteins. Hydrolyzed proteins preferably have a degree of hydrolysis comprised between about 5% and about 90%, preferably between about 5% and about 50%. The degree of hydrolysis corresponds to the number of peptide bonds broken by hydrolysis. The higher this number, the more extensive the hydrolysis.

In particular embodiments of the present invention, the degree of hydrolysis of the hydrolyzed proteins is comprised between about 5% and about 50%, for example between 30% and 40%, between 5% and 20%, or between 5% and 10%, for example 7%.

The protein fraction may also comprise amino acids in a mixture. The mixed amino acids may be natural amino acids, synthetic amino acids or a mixture of natural amino acids and synthetic amino acids.

The mixed amino acids may by themselves form the protein fraction of the anti-regurgitation and/or anti-reflux infant milk according to the present invention. They may also be present beside hydrolyzed proteins and optional non-hydrolyzed proteins.

These hydrolyzed proteins and/or mixed amino acids are more digestible than non-hydrolyzed proteins and allow accelerating gastric emptying. A preferred composition according to the invention, in particular a preferred anti-regurgitation composition not having any effect on the stools, comprises hydrolyzed proteins and mixed amino acids, for example about 95% hydrolyzed proteins for 5% of mixed amino acids.

Thus, a particular composition according to the invention, typically an anti-regurgitation and/or anti-reflux composition, in particular not altering the gut motility of the infant or child and allowing restoring gut motility, comprises a protein fraction containing a majority of hydrolyzed proteins and/or mixed amino acids.

Another particular composition according to the invention, typically another anti-regurgitation and/or anti-reflux composition, in particular not altering gut motility of the infant or child or allowing restoring gut motility, comprises a protein fraction containing a majority of non-hydrolyzed proteins.

Lipids which may typically enter into the composition of the infant milk according to the present invention may be for example selected from milk fat, safflower oil, egg yellow lipids, olive oil, coconut oil, palm oil, soybean oil, sunflower oil, fish oil, oils from algae and/or from mushrooms, palm olein, medium-chain triglycerides, and fatty acid esters selected, for example, from arachidonic acid, linoleic acid, palmitic acid, stearic acid, docosahexanoic acid, eicosapentaenoic acid, linolenic acid, oleic acid, lauric acid, capric acid, caprylic acid and caproic acid.

The carbohydrates which may enter into the composition of the present infant milk (other than the thickeners described later in the present description) may be any ose or oside known to one skilled in the art as being suitable for human nutrition, typically infant nutrition. Typically, the carbohydrates may be selected from lactose, maltodextrins or glucose syrup, sucrose, fructose, and glucose.

Examples of mineral salts, vitamins and other nutrients optionally present in the anti-regurgitation infant milk according to the invention include vitamin A, vitamin B6, vitamin B12, vitamin D, in particular vitamin D3 (cholecalciferol), vitamin E, vitamin K, vitamin C, folic acid, thiamine, inositol, riboflavin, niacin, biotin, pantothenic acid, choline, calcium, phosphorus, iodine, iron, magnesium, copper, zinc, manganese, chlorine, potassium, sodium, selenium, chromium, molybdenum, taurine, and L-carnitine.

In addition to compatibility and stability considerations related to the preparation processes described within the scope of the present invention and the storage conditions of a composition, typically a milk, according to the invention, the presence and amounts of mineral salts and specific vitamins optionally present may slightly change depending on the targeted population (infants (typically from birth to one year old, for example from birth to 6 months old) or young children (typically children less than three years old, for example children 6 to 18 months old)).

The composition, typically the anti-regurgitation and/or anti-reflux composition, in particular not altering the gut motility of the infant or of the child or allowing restoration of gut motility, is advantageously a powder to be reconstituted, i.e., to be dissolved in a beverage (or in any consumable liquid), typically water or milk, for example cow or goat milk, before ingestion by the subject, in particular when said subject has symptoms of regurgitations and/or reflux or may have symptoms of regurgitations (i.e., the large majority of infants and young children).

A particular object of the invention relates to a reconstituted beverage such as a beverage with neutral pH, for example milk reconstituted from a composition according to the invention being a powder.

Typically, a liquid infant milk according to the invention, typically an anti-regurgitation and/or anti-reflux milk, in particular not altering the gut motility of the infant or of the child or allowing restoration of gut motility, comprises a content of said powder infant milk from 11 to 15% by weight, preferably 13% by weight based on the total weight of the reconstituted milk.

Another particular object of the invention relates to a liquid concentrate (prepared from a composition as a powder according to the invention) which may be diluted, preferably by means of a liquid for which the pH is close to neutral.

Typically, a milk according to the invention, in particular an anti-regurgitation and/or anti-reflux milk, preferably not altering the gut motility of the infant or of the child or allowing restoration of gut motility, being a liquid concentrate, prepared from a composition as a powder according to the invention, comprises a content (i.e., a dry material percentage) of said infant milk from 25 to 50% by weight or by mass, preferably 35% by weight or by mass. Such a milk may be diluted in order to obtain a liquid infant milk according to the invention, comprising a content of said powdered infant milk from 11 to 15% by weight or by mass, preferably of 13% by weight or by mass.

Preservation of the concentrated infant milk is advantageously ensured by sterilization in an autoclave and preferentially by a UHT heat treatment followed by aseptic conditioning.

The milks according to the invention may be administered orally or via the enteral route. They are preferentially administered orally since they have, beside their food role, the role for example of preventing, limiting or even suppressing regurgitation and/or reflux symptoms, without altering (while preserving) the gut motility, or even by restoring gut motility.

The composition according to the invention indeed has the significant advantage of being, once it is reconstituted, liquid at pH 7 and viscous at a pH comprised between 6 and 3.5, advantageously as soon as pH=6, typically at a pH comprised between 6 and 5, for example pH=5. It may therefore be used as an anti-regurgitation and/or anti-reflux composition. The composition, the object of the invention, also advantageously preserves the gut motility of the infant as explained in the present text.

In the sense of the present invention, the viscosity of the food bolus is considered satisfactory if it allows reduction, and ideally suppression, of the symptoms of regurgitations and/or reflux.

The viscosity may be measured by a viscosimeter of the Brookfield type, with a disk-shaped (S62) or cylinder-shaped (S61) module and at speeds of rotation comprised between 12 and 100, for example 20 and 100, revolutions per minute. It is also possible to measure the time of flow of a constant volume of product through a calibrated orifice.

Advantageously, the diluted or reconstituted compositions according to the invention have:
  at a pH comprised between 7 and 6.6, a viscosity comprised between 20 and 50 mPa·s, for example between 20 and 45 mPa·s, preferably between 30 and 40 mPa·s; and
  at a pH of less than 6.5, typically between 6 and 3.5, a viscosity comprised between 1,600 and 150 mPa·s, for example at a pH comprised between 6 and 5 a viscosity comprised between 1,600 and 400 mPa·s.

The compounds entering into the formulation of the composition used within the scope of the present invention may be a powder or an aqueous solution. In the sense of the invention, the expressions "aqueous media" or "aqueous solution" respectively refer to a medium or a solution which is at least partly formed with water.

A particular milk according to the invention, typically an anti-regurgitation and/or anti-reflux milk, in particular not altering the gut motility of the infant or child or allowing it to be restored, being a powder, advantageously comprises at least 94% of dry material, preferably at least 95% of dry material, still more preferably at least 98% of dry material by weight based on the total weight of milk as a powder.

Another object of the invention relates to a composition, typically an anti-regurgitation and/or anti-reflux composition, in particular an infant milk, a food supplement for infants or young children, a follow-up milk, a growth milk or a dietetic food for infants or children, characterized in that it preserves the gut motility of the infant or child, for a combined use in the treatment of regurgitation and prevention of anomalies or disorders of gut motility (as defined earlier) of the infant or child or for the sole treatment of anomalies or disorders of gut motility (as defined earlier) of infants or children (i.e., independently of any treatment of the regurgitation and/or reflux problem).

Further another object of the invention relates to a composition, typically an anti-regurgitation and/or anti-reflux composition, in particular an infant milk, a food supplement for infants or young children, a follow-up milk, a growth milk or a dietetic food for infants or children, characterized in that said composition restores the gut motility of the infant or child, for a combined use in the treatment of regurgitation and/or reflux, as well as of anomalies or disorders of gut motility (as defined earlier) of infants or children or for the sole treatment of anomalies or disorders of gut motility (as defined earlier) of infants or children (i.e., independently of any treatment of the regurgitation and/or reflux problem).

The present invention also relates to a process allowing obtaining a composition, typically an anti-regurgitation and/or anti-reflux composition, as a powder, in particular a dietetic or nutritional composition as described earlier, preferably an infant milk, a food supplement for infants, a follow-up milk, a growth milk or a dietetic food, still more preferably an anti-regurgitation and/or anti-reflux infant milk not altering (or preserving, or even restoring) the gut motility of the infant or child, as described earlier.

This process comprises the following steps:

a) preparing a liquid composition base for which the dry material content is of at least 20% by weight (or by mass) based on the total weight of said composition, by mixing with stirring, at a temperature of at least 60° C., constitutive elements of said composition, said elements advantageously comprising cold-soluble carob and pectins, preferably at least two pectins of different natures (still more preferably at least one weakly methylated pectin and at least one highly methylated pectin), the concentration of cold-soluble carob being advantageously less than or equal to about 1% by weight based on the total weight of said composition, b) homogenizing said liquid base obtained at the end of step a) by fractionating the constitutive elements during a first step i) carried out under a pressure preferably comprised between 100 and 300 bars and during a step ii) carried out under a pressure preferably comprised between 10 and 60 bars, c) drying by atomization of the mixture obtained at the end of step b), and d) recovering the composition obtained at the end of step c) as a powder.

The previous process unlike the processes known to this day, allows preparing in a simple and efficient way, from the constitutive elements of a base, typically from an infant milk base in a liquid form, of a composition according to the invention, typically an infant milk, which will be dried and transformed into a powder. The powder obtained at the end of this process is homogeneous, and the reconstituted liquid composition from such a powder has the viscosity properties described earlier, required for limiting, and ideally suppressing, the symptoms of regurgitation and/or reflux, without altering gut motility or even improving it, typically restoring it, when it is altered.

The composition thereby obtained is typically a dietetic food intended for special medical purposes, in particular an anti-regurgitation and/or anti-reflux infant milk not altering gut motility, allowing preserving it, or even ideally improving it when it is altered, the liquid base of which, used for preparing it, is typically a liquid base of a dietetic food intended for special medical purposes, in particular a liquid base of infant milk.

In another embodiment, the constitutive elements of the composition further comprise pre-cooked and/or pre-gelatinized starch.

In another particular embodiment, the dry material content of the liquid base is of at least 35% by weight based on the total weight of the liquid base.

The composition as a powder according to the invention may further advantageously be a pasteurized (or sterilized) composition.

The compositions according to the invention are particularly suitable for use in infants or children to whom a proton pump inhibitor (IPP) is administered, for example selected from Omeprazole, Esomeprazole, Lansoprazole, Pantoprazole and Rabeprazole.

In the sense of the present invention, pasteurization designates a heat treatment step causing destruction of germs considered as pathogens for the subject for which the composition is intended, and more generally a reduction of bacterial flora.

Conventionally, the heat treatment is carried out at a temperature comprised between about 60° C. and about 110° C. for a sufficient time in order to obtain pasteurization, i.e., for a period comprised between about 15 minutes and a few seconds, for example about 25 or 30 seconds. One skilled in the art is able to determine the period suitable for a given temperature which will allow the desired pasteurization to be obtained without destroying the composition, its nutritional properties or its anti-regurgitation and/or reflux properties. Regarding milk in particular, one skilled in the art is able to determine the suitable conditions for preserving the proteins and vitamins.

The process described earlier may thus further advantageously comprise an additional step for applying, to the liquid base obtained at the end of step a) or at the end of step b), a heat treatment at a temperature comprised between 60° C. and 110° C. for a sufficient period in order to pasteurize the liquid base. This process thus allows obtaining a composition, typically an anti-regurgitation and/or anti-reflux pasteurized composition, as a powder not altering gut motility.

Such a composition does not have any microbiological risks (notably for *C. sakazakii*) observed during dry mixtures of an infant milk base with starch or carob powder.

A particular object of the present invention thus relates to a process or a method allowing preparation of a pasteurized composition as a powder, in particular a nutritional, anti-regurgitation and/or anti-reflux composition for infants or children, and/or not altering or allowing restoration of gut motility of said infant or child, in particular of an infant milk or a dietetic composition as described earlier, comprising the following steps:

a) preparing a liquid composition base for which the dry material content is of at least 20% by weight (or by mass) based on the total weight of said composition, by mixing, with stirring, at a temperature of at least 60° C., the constitutive elements of said composition, said elements advantageously comprising cold-soluble carob and pectins, preferably at least two pectins of different natures (still more preferably at least one weakly methylated pectin and at least one highly methylated pectin), the concentration of cold-soluble carob being advantageously less than or equal to about 1% by weight based on the total weight of the said composition, b) homogenizing the liquid base obtained at the end of step a) by fractionation of the constitutive elements during a first step i) carried out under a pressure preferably comprised between 100 and 300 bars and during a step ii) carried out under a pressure preferably comprised between 10 and 60 bars, c) applying, to the liquid base obtained at the end of step a) or at the end of step b), a heat treatment at a temperature comprised between 60° C. and 110° C. for a sufficient time for pasteurizing said base, d) drying by atomization of the mixture obtained at the end of step c), and e) recovering the pasteurized composition as a powder obtained at the end of step d).

Step a) for preparing a liquid base comprises the mixing, with stirring, of the components, ingredients or elements of interest, as described earlier, making up the composition.

Producing a liquid mixture requires the dilution of each ingredient in water.

The ingredients (the base of the composition, for example an infant milk base or a dietetic composition base, and thickener(s)) may be mixed as powders and subsequently put into solution. They may also be mixed as solutions. It is also possible to add one of the components as a powder to the other component in solution. In such a case, it is preferable to maintain the component in solution with stirring during the mixing with the component as a powder in order to limit or reduce, and ideally avoid, formation of agglomerates during mixing.

Thus, the aqueous nature of the mixture obtained at the end of step a) may come from the liquid form of the thickeners, from the liquid form of the base used and/or from the addition of water to the mixture of the products used as a powder.

A stirrer or mixing unit, for example a mixing pump, a de-flocculator, or a mixer equipped with a rotor/stator system, may advantageously be used for dissolving the various ingredients and facilitating the obtaining of a homogeneous base.

The preferred use of a mixer of suitable shape and size also allows avoiding excessive incorporation of air into the liquid base, in particular the milk base.

One skilled in the art moreover will be able to adapt the speeds of rotation in order to further reduce such an excessive incorporation of air into the liquid base.

The mixing step a) is preferably carried out at a temperature of at least 60° C., for example comprised between about 60° C. and 90° C. or between about 60° C. and 80° C., still more preferentially between about 70° C. and 75° C. Typically, the temperature is 75° C.

In a preferred embodiment, the liquid base obtained at the end of step a) is maintained with stirring until application of the homogenization step, for example by means of a device as described earlier.

The step for homogenization of the mixed, optionally pasteurized, liquid base obtained at the end of step a) of the process according to the invention allows fractionation of the constitutive elements of said base. The homogenization comprises two compression steps intended to reinforce the stability of this base. The first fractionation step i) is preferably carried out under a pressure comprised between about 100 bars and about 300 bars, and the second step ii) being preferably carried out under a pressure comprised between about 10 bars and about 60 bars.

This step is advantageously applied on a two-stage homogenizer.

The homogenization pressure of the first stage of said homogenizer is thus typically comprised between about 100 bars and about 300 bars, preferably between about 150 bars and about 300 bars, still more preferentially between about 170 bars and about 200 bars.

The homogenization pressure of the second stage is typically comprised between about 10 bars and about 60 bars, preferably between about 30 bars and about 60 bars, still more preferentially between about 30 bars and about 40 bars.

The pasteurization step, optionally present in the preparation process according to the invention, provides the application to the mixture obtained at the end of step a) or at the end of the homogenization step of a heat treatment comprised between about 70° C. and about 110° C., preferably between 70° C. and 100° C., between 75° C. and 100° C., between 75° C. and 95° C., between 80° C. and 95° C. or between 85° C. and 95° C., even more preferentially between 80° C. and 90° C., for a sufficient time for inactivating and destroying at least the germs considered as pathogens (notably *C. sakazakii*).

Typically, the heat treatment of the pasteurization step is applied for at least 2 minutes, and preferably at most 10 minutes, when the temperature is equal to or less than 80° C., for example comprised between 75° C. and 60° C., and for at least 25 seconds, typically at least 1 minute, and preferably at most 5 minutes, when the temperature is equal to or greater than 85° C., for example comprised between 85° C. and 100° C.

The treatment may also be applied for a period of more than 2 minutes, and preferably less than 10 minutes, when the temperature is 75° C., for a period comprised between about 2 minutes and about 3 minutes when the temperature is 80° C., for a period comprised between about 1 minute and about 2 minutes when the temperature is 90° C., for a period of about 1 minute when the temperature is 95° C., and for less than 30 seconds, typically 25 seconds, when the temperature is 100° C.

The mixture, either pasteurized or not, obtained at the end of the homogenization step of the process according to the invention is advantageously dried by atomization in order to obtain a composition as a powder comprising, as explained earlier, a dry extract comprised between 85% and 99%, preferably a dry extract of at least 94% or at least 95%, still more preferentially of at least 98% based on the total weight of milk as a powder.

The mixture, either pasteurized or not, obtained at the end of the homogenization step of the process according to the invention is typically introduced to the top of an atomization tower. The mixture is then "atomized" (transformed into an aerosol or mist) by means of an atomization turbine or by high-pressure injection through one or several nozzles. Advantageously, the atomization is carried out under a pressure comprised between 120 and 230 bars, preferably between 135 and 195 bars. The droplets thereby formed are carried away and dehydrated by a hot air stream, the temperature of which is typically comprised between 160° C. and 240° C., preferably between 180° C. and 220° C. The droplets are dried into a powder before falling on the lower walls of the apparatus. Powder/humid air separation is obtained for example by means of cyclone separators, the use of which is well-known to one skilled in the art.

When it is desired to obtain a powder composition according to such a process, dehydration in the atomization tower should preferably not be complete. The residual humidity present in the powder composition may for example be comprised between 6 and 14% at the bottom of the chamber. This residual humidity allows limited and controlled agglomeration of the particles which leads to the formation of granules with a porous structure.

Dehydration may then be completed in additional devices of the fluidized-bed dryer type. The powder may then be cooled inside a vibro-fluidized bed.

The claimed invention is illustrated in a non-limiting way by the figures and examples below.

LEGEND OF THE FIGURES

FIG. 1:

A—table of the viscosity of the composition versus pH

B—viscosity graph of the composition according to the invention versus pH

EXAMPLES

Example 1

Formulation

The formulation of milks intended for infant feeding is most often strictly restricted by legislation setting composition standards. Depending on the countries, there may be differences of appreciation notably because of local specificities in the practice of food diversification or else minor modifications of the nutritional optima resulting from locally conducted investigations or studies. Under these conditions, the present example does not intend to represent the diversity of the thickened milk formulations according to the invention.

Conventionally, in order to meet the nutritional needs of infants, infant milks comprise about 10-15% of proteins, about 25% of lipids and about 50-65% of carbohydrates as well as minerals, vitamins and optionally growth factors. Other ingredients such as one or several prebiotics and/or probiotics may moreover be added to infant milks.

A non-limiting example of a composition of the anti-regurgitation and/or anti-reflux infant milk type preserving gut motility according to the invention is provided in Table I below.

TABLE I

| Composition/Nutritional profile: | | For 100 g of powder | For 100 ml of 13% reconstituted milk |
|---|---|---|---|
| Proteins Nx 6.25 | g | 12.1 | 1.57 |
| Lipids | g | 25.1 | 3.26 |
| Carbohydrates | g | 53 | 6.89 |
| Maltodextrins | g | 26 | 3.38 |
| Lactose | g | 22 | 2.86 |
| Starch | g | 0.9 | 0.12 |
| Dextrose | g | 3.4 | 0.44 |
| HM pectin | g | 1 | 0.13 |
| Amidated LM pectin | g | 4.25 | 0.55 |
| Cold-soluble carob | g | 0.5 | 0.07 |
| Energy | kcal | 493.7 | 64.18 |
| Minerals | | | |
| Sodium | mg | 180 | 23.40 |
| Potassium | mg | 520 | 67.60 |
| Chlorine | mg | 345 | 44.85 |
| Calcium | mg | 460 | 59.80 |
| Phosphorus | mg | 340 | 44.20 |
| Magnesium | mg | 45 | 5.85 |
| Iron | mg | 6 | 0.78 |
| Zinc | mg | 3.5 | 0.46 |
| Iodine | µg | 55 | 7.15 |
| Copper | µg | 350 | 45.50 |
| Manganese | µg | 45 | 5.85 |
| Selenium | µg | 9 | 1.17 |
| Chromium | µg | <45 | <5.85 |
| Molybdenum | µg | <45 | <5.85 |
| Fluorine | µg | <450 | <58.5 |
| Vitamins | | | |
| A | µg RE | 450 | 58.50 |
| B1 | µg | 400 | 52.00 |
| B2 | µg | 800 | 104.00 |
| B6 | µg | 300 | 39.00 |
| B12 | µg | 1.5 | 0.20 |
| C | mg | 60 | 7.80 |
| D | µg | 7.5 | 0.98 |
| E | IU | 16.4 | 2.13 |
| K1 | µg | 30 | 3.90 |

TABLE I-continued

| Composition/Nutritional profile: | | For 100 g of powder | For 100 ml of 13% reconstituted milk |
|---|---|---|---|
| Biotin | µg | 15 | 1.95 |
| Niacin | mg | 4.5 | 0.59 |
| Folic acid | µg | 60 | 7.80 |
| Pantothenic acid | mg | 2.4 | 0.31 |
| Choline | mg | 60 | 7.80 |
| Inositol | mg | 30 | 3.90 |
| Taurine | mg | 44 | 5.72 |
| L-carnitine | mg | 8 | 1.04 |

In the present composition, the starch, in particular the pre-cooked and/or pre-gelatinized starch present at a low content, has no influence on the effectiveness of the formula, in particular on its viscosity.

Indeed, upon manufacturing the compositions according to the invention, the starch, in particular the pre-cooked and/or pre-gelatinized starch, when it is present, undergoes, like all of the ingredients making up the composition, in particular the liquid base, a step for heating to a temperature of at least 60° C., followed by homogenization by fractionation of the constitutive elements of the composition, in particular the liquid base, during a first step i) carried out under a pressure comprised between 100 and 300 bars and a step ii) carried out under a pressure comprised between 10 and 60 bars. Such treatments inhibit or suppress any capability of the starch to thicken and to impact the viscosity of the compositions according to the invention which would comprise starch.

Example 2

Process for Manufacturing a Pasteurized Infant Milk as a Powder Comprising i) Cold-Soluble Carob and ii) at Least Two Pectins of Different Natures The infant milk base comprising 37% of dry extract is prepared by mixing water heated beforehand to 70° C. with the different infant milk ingredients (said ingredients comprising proteins or amino acids+cold-soluble carob+weakly esterified pectins or weakly esterified and amidated pectins+highly esterified pectins+carbohydrates+minerals+plant fats+vitamins+growth factors). The carob and pectins are incorporated into the infant milk base maintained with stirring in order to obtain their complete dissolution. The whole is maintained at 70° C. with stirring in a double-walled chamber until the homogenization step. The infant milk base then undergoes dual effect homogenization at 200/40 bars, i.e., a first homogenization step is carried out under a pressure of 200 bars and a second homogenization step is carried out under a pressure of 40 bars. The homogenized infant milk base is then preferably pasteurized by heat treatment at about 80° C. for 1 to 2 minutes with the purpose of removing bacteriological risks, in particular those related to *Cronobacter sakazakii*.

The infant milk base, preferably pasteurized, then undergoes an atomization step carried out under a pressure of 190 bars which allows obtaining droplets with a sufficiently small diameter so as to be dried with air, the temperature of which at the inlet of the chamber is 185° C. and the temperature at the outlet of the chamber is 94° C.

The applied process here allows obtaining a throughput of 1,000 and 2,000 kg of powder/hour.

The reconstituted liquid milk (ready to be consumed) obtained from this infant milk powder has a dry extract of about 13% in the baby bottle. The viscosity of this reconstituted milk, measured at 60 rpm (revolutions per minute), at 37° C., is comprised between 25-45 mPa·s (S61 mobile) at a pH close to neutral and comprised between 1,502 and 145 mPa·s for a pH ranging from 6 to 3.5. The reconstituted liquid milk contains 0.68% of pectins and 0.065% of carob in the baby bottle.

Example 3

Comparison Between the Viscosity of a Reconstituted Milk Comprising a Milk in Powder Form According to the Invention with the Viscosity of a Conventional AR Milk Containing Starch (Novalac AR®)

An infant milk according to the invention is produced and collected as a powder according to the manufacturing process mentioned in Example 2. This milk according to the invention thus comprises 4.25% of weakly esterified pectins and weakly esterified and amidated pectins, 1% of highly esterified pectins and 0.5% of cold-soluble carob.

Method and Tools

The liquid infant milk is then prepared, by dilution of the infant milk as a powder according to the invention in hot water (at 60° C.) with 13% of dry extract. Said liquid infant milk is then cooled to 37° C.

The conventional AR milk based on starch is also prepared by diluting the powder in water (also at 37° C.) with 13% of dry extract.

The viscosities of both products are then measured by means of a Brookfield viscosimeter (DV-I Prime) at the reconstitution pH (close to neutral) with an S61 mobile at 60 rpm (revolutions per minute) and at a temperature of 37° C.

Hydrochloric acid, with a molarity equal to 1 (HCl 1M), is added to both reconstituted products in order to attain a pH of 5.5. The viscosities of both acidified products are then measured at 37° C., with an S61 mobile and at a rate of 60 rpm for the Novalac AR® product and with an S62 mobile and at a rate of 30 rpm for the infant milk formula according to the invention.

Then hydrochloric acid, with a molarity equal to 1 (HCl 1M), is again added to both reconstituted products in order to attain a pH of 3.5. The viscosities of both acidified products are then again measured at 37° C., with an S62 mobile and at a rate of 60 rpm.

TABLE 3

| | Viscosities in mPa · s | | |
|---|---|---|---|
| AR products | Neutral pH | pH = 5.5 | pH = 3.5 |
| Novalac AR ® | 10 | 96 | 241 |
| Infant milk according to the invention | 36 | 645 | 145 |

Conclusion:

The significant increase in viscosity, observed as soon as pH=6, in particular at pH=5.5, of the infant milk according to the invention will provide significant effectiveness against regurgitations and/or reflux of the infant or child. Indeed, the pH of the stomach of the infant 15 mins after ingestion of a milk is generally found to be between 6 and 5. Therefore it is actually seen that conventional Novalac AR® milk, for which the viscosity is of about 100 mPa·s, will have a lesser effect on regurgitations and/or reflux: the more viscous the product, the more the regurgitations and/or reflux will decrease.

Example 4

Comparison Between the Viscosity of a Reconstituted Milk Comprising a Milk as a Powder According to the Invention with the Viscosity of an AR Milk Containing Starch and Cold-Soluble Carob (Novalac AR Digest®)

An infant milk according to the invention is produced and collected as a powder according to the manufacturing process mentioned in Example 2. This milk according to the invention thus contains 4.25% of weakly esterified pectins and weakly esterified and amidated pectins, 1% of highly esterified pectins and 0.5% of cold-soluble carob.

Method and Tools

The liquid infant milk according to the invention is then produced, by diluting the infant milk as a powder according to the invention in hot water (at 60° C.) with 13% of dry extract. Said liquid infant milk is then cooled to 37° C.

The AR-Digest® milk based on starch and on cold-soluble carob is also prepared by diluting the powder in water (also at 37° C.) with 13% of dry extract.

The viscosities of both products are then measured by means of a Brookfield viscosimeter (DV-I Prime) at the reconstitution pH (close to neutral) with an S61 mobile at 60 rpm (revolutions per minute) and at a temperature of 37° C.

Hydrochloric acid, with a molarity equal to 1 (HCl 1M), is added to both reconstituted products in order to attain a pH of 5.5. The viscosities of both acidified products are then measured at 37° C., with an S62 mobile at a rate of 60 rpm for the Novalac AR-Digest® product and at a rate of 30 rpm for the infant milk formula according to the invention.

Then hydrochloric acid, with a molarity equal to 1 (HCl 1M), is again added to both reconstituted products in order to attain a pH of 3.5. The viscosities of both acidified products are then again measured at 37° C., with an S62 mobile and at a rate of 60 rpm.

TABLE 4

| | Viscosities in mPa · s | | |
|---|---|---|---|
| AR products | pH neutral | pH = 5.5 | pH = 3.5 |
| Novalac AR Digest ® (hydrolyzed proteins + cold-soluble carob (4%)) | 18 | 108 | 210 |
| Infant milk according to the invention | 36 | 645 | 145 |

Conclusion

Like in Example 3, it is seen here that the infant milk according to the invention allows greater effectiveness as to the decrease of regurgitations and/or reflux of the infant or child at pHs comprised between 6 and 5 (pH of the infant's stomach about 15 minutes after ingesting an infant milk).

Example 5

Comparison Between the Viscosity of a Reconstituted Milk Comprising a Milk as a Powder According to the Invention Obtained by Dry Mixing with the Viscosity of a Conventional AR Milk Thickened by Means of Starch and Cold-Soluble Carob (Novalac AR Digest®)

An infant milk base is produced and collected as a powder at the outlet of the drying tower. To this base as a powder are then added, by dry mixing, 4.25% of weakly esterified pectins or weakly esterified and amidated pectins, 1% of highly esterified pectins and 0.5% of cold-soluble carob.

Method and Tools

The liquid infant milk is then produced by diluting the infant milk as a powder according to the invention in hot water (at 60° C.) with 13% of dry extract. Said liquid infant milk is then cooled to 37° C.

The AR-Digest® milk based on starch and cold-soluble carob is also prepared by diluting the powder in water (also at 37° C.) with 13% of dry extract.

The viscosities of both products are then measured by means of a Brookfield viscosimeter (DV-I Prime) at the reconstitution pH (close to neutral) with an S61 mobile at 60 rpm (revolutions per minute) and at a temperature of 37° C.

Hydrochloric acid with a molarity equal to 1 (HCl 1M) is added to both reconstituted products in order to attain a pH of 5.5. The viscosities of both acidified products are then measured at 37° C., with an S62 mobile at a rate of 60 rpm for the Novalac AR-Digest® product and at a rate of 30 rpm for the infant milk formula according to the invention.

Next, hydrochloric acid, with a molarity equal to 1 (HCl 1M), is again added to both reconstituted products in order to attain a pH of 3.5. The viscosities of both acidified products are then again measured at 37° C., with an S62 mobile and at a rate of 60 rpm.

TABLE 5

| AR products | Viscosities in mPa · s | | |
|---|---|---|---|
| | neutral pH | pH = 5.5 | pH = 3.5 |
| Novalac AR Digest ® (cold-soluble carob (4%) + starch) | 18 | 108 | 210 |
| Infant milk according to the invention obtained by dry mixing | 25 | 530 | 125 |

Conclusion

Like in the previous example, the infant milk according to the invention allows greater effectiveness as to the reduction of regurgitations and/or reflux of the infant or child at a pH comprised between 6 and 5 (pH of the stomach of the infant 15 minutes after ingestion of an infant milk).

Example 6

Evaluation of the Clinical Effectiveness on Regurgitations and the Effect on Gut Motility of a Reconstituted Milk Obtained from a Composition as a Powder According to the Invention An open clinical study was conducted in order to determine the influence of a reconstituted milk obtained from a composition, typically from a milk, as a powder according to the invention on the frequency and intensity of the episodes of regurgitations and/or refluxes as well as on gut motility, in particular on the consistency of the stools of infants. This clinical study was conducted over a period of 14 days plus or minus 2 days, i.e., over a period ranging from 12 to 16 days between the day of the first visit or inclusion day, noted as D0, and the day of the second visit, about 14 days later, at plus or minus two days, noted as D14.

Method and Tools

A composition according to the invention for which the nutritional profile corresponds to that of Table II below was prepared and collected as a powder.

TABLE II

| Composition/Nutritional profile: | | For 100 g of powder | For 100 ml of 13% reconstituted milk |
|---|---|---|---|
| Proteins Nx 6.25 | g | 12.1 | 1.57 |
| Lipids | g | 25.1 | 3.26 |
| Carbohydrates | g | 53 | 6.89 |
| HM pectin | g | 1 | 0.13 |
| Amidated LM pectin | g | 4.25 | 0.55 |
| Cold-soluble carob | g | 0.5 | 0.07 |
| Energy | kcal | 493.7 | 64.18 |
| Minerals | | | |
| Sodium | mg | 180 | 23.40 |
| Potassium | mg | 520 | 67.60 |
| Chlorine | mg | 345 | 44.85 |
| Calcium | mg | 460 | 59.80 |
| Phosphorus | mg | 340 | 44.20 |
| Magnesium | mg | 45 | 5.85 |
| Iron | mg | 6 | 0.78 |
| Zinc | mg | 3.5 | 0.46 |
| Iodine | µg | 55 | 7.15 |
| Copper | µg | 350 | 45.50 |
| Manganese | µg | 45 | 5.85 |
| Selenium | µg | 9 | 1.17 |
| Chromium | µg | <45 | <5.85 |
| Molybdenum | µg | <45 | <5.85 |
| Fluorine | µg | <450 | <58.5 |
| Vitamins | | | |
| A | µg RE | 450 | 58.50 |
| B1 | µg | 400 | 52.00 |
| B2 | µg | 800 | 104.00 |
| B6 | µg | 300 | 39.00 |
| B12 | µg | 1.5 | 0.20 |
| C | mg | 60 | 7.80 |
| D | µg | 7.5 | 0.98 |
| E | IU | 16.4 | 2.13 |
| K1 | µg | 30 | 3.90 |
| Biotin | µg | 15 | 1.95 |
| Niacin | mg | 4.5 | 0.59 |
| Folic acid | µg | 60 | 7.80 |
| Pantothenic acid | mg | 2.4 | 0.31 |
| Choline | mg | 60 | 7.80 |
| Inositol | mg | 30 | 3.90 |
| Taurine | mg | 44 | 5.72 |
| L-carnitine | mg | 8 | 1.04 |

For this, an infant milk base comprising 37% of dry extract is prepared by mixing water heated beforehand to 70° C. with the different ingredients of the infant milk (said ingredients comprising proteins or amino acids+cold-soluble carob+weakly esterified pectins or weakly esterified and amidated pectins+highly esterified pectins+carbohydrates+minerals+plant fats+vitamins+growth factors). The carob and the pectins are incorporated into the infant milk base maintained with stirring in order to obtain their complete dissolution. The whole is maintained at 70° C. with stirring in a double-walled chamber until the homogenization step. The infant milk base is then pasteurized by heat treatment at about 80° C. for 1 to 2 minutes with the purpose of suppressing bacteriological risks, in particular those related to *Cronobacter sakazakii*. The pasteurized infant milk base is then subjected to dual effect homogenization at 200/40 bars, i.e., a first homogenization step is carried out under a pressure of 200 bars and a second homogenization step is carried out under a pressure of 40 bars.

The pasteurized and homogenized infant milk base then preferably undergoes an atomization step carried out under a pressure of 140 bars which allows obtaining droplets with a sufficiently small diameter so as to be dried with air, the temperature of which at the inlet in the chamber is 185° C. and the temperature at the outlet of the chamber is comprised between 80 and 105° C., in particular equal to 94° C.

The applied process here allows obtaining a throughput of 1,000 and 2,000 kg of powder/hour.

The obtained composition as a powder is then conditioned in boxes. This composition according to the invention thus comprises 4.25% of weakly esterified and amidated pectins, 1% of highly esterified pectins and 0.5% of cold-soluble carob.

The concentration of non-hydrolyzed proteins is advantageously of about 9% by weight (preferably about 7.2% of whole caseins and 1.8% of soluble whole proteins) and the concentration of hydrolyzed proteins is advantageously of about 3% by weight (preferably exclusively soluble proteins), based on the total weight of the composition.

In order to be estimated as admissible for this study, the infants should be at most 5 months old, be exclusively fed with an infant formula, have at least 5 regurgitation episodes per day, not have started food diversification and have no new food introduced into their diet in the 2 weeks following the inclusion.

In order to be estimated as admissible for this study, the infants should also not reproduce any of the following non-inclusion criteria:

be fed with mother's milk,
have complicated gastro-esophageal reflux (GOR) symptoms such as nausea, dysphagia, growth retardation, or obvious signs of esophagitis,
have intestinal disorders such as, notably, gastroenteritis or chronic diarrhea,
have received medical treatment for regurgitations during the week preceding the inclusion (such as Omeprazole or Ranitidine), or be required to begin such a treatment,
have received antibiotics during the week preceding the inclusion or require antibiotherapy,
have an allergy to cow milk proteins, or have an increased risk of allergy to cow milk proteins,
have a situation which according to the investigator may interfere with the conduct of the study or have a particular risk for them, or
be participating in another clinical study.

100 admissible infants were recruited. Of these 100 initially recruited infants, 10 infants were excluded before D14 for reasons such as a change in opinion of the parents, suspicion of allergy to cow milk proteins, resuming breast-feeding, having lost sight of the patient, a formula a priori rejected because of its taste, suspicion of complicated GOR and suspicion of gastroenteritis. The shown results are those associated with 90 infants included before D14, which represents 100% of the evaluated cases.

The main criterion studied during this clinical study was the frequency of regurgitations, in particular the number of regurgitations per day. The regurgitations were also evaluated by means of the Vandenplas score, defined in the following way:

Score=0: Less than 2 regurgitation episodes per day.
Score=1: At least 3 and at most 5 regurgitation episodes of a small volume per day (less than a teaspoon per day, i.e., less than about 5 ml).
Score=2: More than 5 regurgitation episodes per day, the volume of which is greater than that of a teaspoon.
Score=3: More than 5 regurgitation episodes per day of about half the volume of the consumed baby bottle for less than half of the consumed baby bottles.
Score=4: Continuous regurgitations of small volumes for more than 30 minutes after each baby bottle.
Score=5: Regurgitations of at least half the volume of the consumed baby bottle for at least half of the consumed baby bottles.
Score=6: Regurgitation of the total volume of the consumed baby bottle after each baby bottle.

The Vandenplas score was used in several clinical studies to this day and is described in many scientific publications, notably in "Vandenplas Y, Hachimi-Idrissi S, Casteels A, Mahler T, Loeb H. *A clinical trial with an "anti-regurgitation" formula.* Eur J Pediatr. 1994; 153(6): 419-23".

One skilled in the art is aware of other scales evaluating the intensity of regurgitations, in particular the volume and/or the frequency of the regurgitations, such as Orenstein's score described in "Orenstein S R, Magill H L, Brooks P. *Thickening of infant feedings for therapy of gastroesophageal reflux.* J Pediatr 1987; 110: 181-6".

The effect on the transit was measured by evaluating the average consistency of the stools of the infants, to be selected from hard stools, formed stools, soft or liquid stools.

During a first medical examination on day D0, the parents of the 100 infants signed an informed consent form, and each of the 100 infants included in the study was examined by a pediatrician-investigator who filled an observation report in which various data were reported, in particular the average number of regurgitations per day, the average consistency of the stools and the average Vandenplas score over the 3 days preceding the medical examination.

During this first examination, the pediatrician handed over to the parents boxes of reconstituted milk comprising a milk as a powder according to the invention in a sufficient amount for covering the needs of the infant for 2 weeks. The reconstituted milk comprising a milk as a powder according to the invention contained in these boxes was the only food of the infants during the whole period of the study.

During the whole period of the study and for each baby bottle preparation, the parents were instructed to prepare the liquid infant milk by diluting the infant milk as a powder according to the invention in water at 40° C. with 13% of dry extract and letting it cool subsequently to about 37° C. They were also instructed not to change the food habits of the infant and to continue to feed it as usual. Typically, they were instructed not to change the number or the volume of the baby bottles and to observe the food requests from the infant.

At D14, i.e., about 14 days after inclusion, at plus or minus 2 days, a second medical examination took place for the 90 infants included before D14. During this examination, the pediatrician-investigator completed the observation report in which were reported various data, in particular the average number of regurgitations per day, the average consistency of the stools and the average Vandenplas score over the 3 days preceding the medical examination.

Frequency of the Regurgitations

Information from the observation reports of the pediatrician-investigator relating to the average number of regurgitations per day at D0 and at D14 for the 90 infants included before D14 was listed in Table 6 below.

TABLE 6

| | Number of regurgitations per day | |
|---|---|---|
| | Inclusion = D0 | D14 |
| Average | 7.3 | 1.06 |
| Standard deviation | 3.4 | 1.25 |
| Minimum | 5 | 0 |
| Maximum | 20 | 5 |

A reduction in the number of regurgitations was also observed between D0 and D14 in 100% of the evaluated cases. While 100% of the evaluated infants had at least 5 regurgitation episodes per day at D0, 70% of these infants had less than 0 or 1 regurgitation episode per day at D14.

Conclusion

These data confirm the effectiveness of a reconstituted milk comprising a composition as a powder according to the invention at reducing of the number of regurgitations and/or refluxes of the infant per day.

Intensity of the Regurgitations

Information from the observation reports of the pediatrician-investigator relating to the average Vandenplas score at D0 and at D14 for the 90 infants included before D14 indicates a reduction in the Vandenplas score in 99% of the cases.

A reduction in the average value of the Vandenplas score was also observed between D0 and D14 which passes from 1.9 to 0.2, as indicated in Table 7 below.

At D14, 77 infants, i.e., 85.5% of the 90 included infants, have a Vandenplas score of 0 and therefore have less than 2 regurgitation episodes per day.

TABLE 7

|  | Vandenplas score | |
| --- | --- | --- |
|  | Inclusion = D0 | D14 |
| Average | 1.9 | 0.2 |
| Standard deviation | 0.8 | 0.6 |

Conclusion

These data confirm the effectiveness of a reconstituted milk comprising a milk as a powder according to the invention at reducing of the intensity of the regurgitations and/or refluxes of the infant.

Gut Motility (Intestinal Transit)

Information from the observation reports of the pediatrician-investigator relating to the average consistency of the stools at D0 and at D14 for the 90 infants included before D14 has been listed in Table 8 below.

TABLE 8

|  | Consistency of the stools | |
| --- | --- | --- |
|  | Inclusion | D14 |
| Hard | 14.40% | 3.40% |
| Formed | 36.70% | 51.10% |
| Soft to liquid | 48.90% | 45.50% |

Conclusion

These data confirm that a reconstituted milk comprising a milk as a powder according to the invention does not alter the gut motility of the infant, and typically does not cause any undesirable effects on the stools, such as the percentage increase in constipation, diarrhea, or hard, soft, liquid and/or too frequent stools observed within the population of tested children.

These data also show an improvement or even a standardization of the consistency of stools between D0 and D14 as illustrated by a reduction of the percentage of infants having hard, soft or liquid stools and an increase in the percentage of infants having formed stools. The infant milk according to the invention therefore allows restoring gut motility in infants, i.e., it is capable of re-establishing normal transit, preferably of the formed stools, for these patients when the latter is altered.

The composition as a powder according to the invention does not alter, preserves, or even restores gut motility of the subject to which it is administered.

The infant milk according to the invention is therefore effective as an anti-regurgitation and/or anti-reflux milk, both as regards the frequency of the regurgitations and/or reflux and as regards their intensity, and without altering gut motility, typically avoiding that the infants be subject to the inconveniences associated with an alteration of transit such as constipation, soft stools, liquid and/or too frequent stools (diarrhea), and/or colic, or even restoring gut motility of said infants.

We claim:

1. A method for treating regurgitation and/or reflux and improving or maintaining gut motility, the method comprising administering to an infant or a child an effective amount of a nutritional composition comprising cold-soluble carob and at least two pectins of different natures.

2. The method of claim 1, wherein the nutritional composition is a milk for infants or children.

3. The method of claim 2, wherein the milk for infants or children is a powder milk.

4. The method of claim 1, wherein gut motility anomalies or disorders comprise constipation, soft stools, diarrhea, colics.

5. The method of claim 1, wherein cold-soluble carob has solubility of more than 60% in an aqueous medium at a temperature between 10° C. and 45° C.

6. The method of claim 1, wherein the concentration of cold-soluble carob is less than or equal to about 1% by weight based on the total weight of the composition.

7. The method of claim 1, wherein the pectins are highly methylated, weakly methylated pectins, or a mixture of both.

8. The method of claim 1, wherein the composition further comprises starch.

9. The method of claim 1, wherein the composition further comprises carbohydrates, said carbohydrates being lactose and/or maltodextrins; lipids; proteins, said proteins being either hydrolyzed or unhydrolyzed; and/or amino acids.

10. The method of claim 1, wherein the composition has a viscosity between 1,600 mPa·s and 150 mPa·s when the pH is between 6 and 3.5.

11. The method of claim 1, wherein the composition comprises cold-soluble carob at a percentage of less than about 1% by weight; weakly methylated amidated pectins at a concentration between about 4% and about 5% by weight; highly methylated pectins at a concentration of about 1% by weight; said percentages being expressed by weight based on the total weight of the composition.

* * * * *

UNITED STATES PATENT AND TRADEMARK OFFICE
CERTIFICATE OF CORRECTION

PATENT NO. : 9,642,391 B1
APPLICATION NO. : 15/399767
DATED : May 9, 2017
INVENTOR(S) : Jonathan Albert Margossian and Nicolas Pradeau It is certified that error appears in the above-identified patent and that said Letters Patent is hereby corrected as shown below:

In the Specification

Column 2
Line 45, "(Cane et al.," should read --(Carré et al.,--.

Column 12
Line 38, "a 1-4 bonds" should read --α 1-4 bonds--.

Column 12
Lines 39-40, "a 1-4 bonds and a 1-6 branches" should read --α 1-4 bonds and α 1-6 branches--.

Signed and Sealed this
Twenty-ninth Day of May, 2018

Andrei Iancu
*Director of the United States Patent and Trademark Office*